(12) United States Patent
Björe et al.

(10) Patent No.: US 6,492,382 B1
(45) Date of Patent: Dec. 10, 2002

(54) DRIED OR FROZEN PHARMACEUTICAL PREPARATION CONTAINING A CLASS III ANTIARRHYTHMIC COMPOUND

(75) Inventors: Annika Björe, Stenungsund (SE); Anna-Karin Granath, Partille (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/423,200

(22) PCT Filed: Oct. 11, 1999

(86) PCT No.: PCT/SE99/01828

§ 371 (c)(1), (2), (4) Date: Nov. 3, 1999

(87) PCT Pub. No.: WO00/21533

PCT Pub. Date: Apr. 20, 2000

(30) Foreign Application Priority Data

Oct. 15, 1998 (SE) .............................................. 9803517

(51) Int. Cl.$^7$ ............................................. A61K 31/439
(52) U.S. Cl. ....................................... 514/300; 514/821
(58) Field of Search .................................. 514/300, 821

(56) References Cited

U.S. PATENT DOCUMENTS 6,291,475 B1 * 9/2001 Alstermark et al. ........ 514/300

FOREIGN PATENT DOCUMENTS

| EP | 0236679 | 9/1987 |
|----|---------|--------|
| WO | 9931100 | 6/1999 |
| WO | 0021533 | 4/2000 |

OTHER PUBLICATIONS

The Cardiac Arrhythmia Suppression Trial Investigators (Aug. 10, 1989) Effect of encainide and flecainide on mortality in a randomized trial of arrhythmia suppression after myocardial infarction, The New England Journal of Medicine, vol. 321, No. 6, p. 406–412.

Remington's Pharmaceutical Sciences, Fifteenth Edition, Merck Printing Company, 1975, pp. 1461–1467 and 1482–1485.*

* cited by examiner

Primary Examiner—Frederick Krass
(74) Attorney, Agent, or Firm—White & Case LLP

(57) ABSTRACT

The present invention relates to dried preparations containing a class III antiarrhythmic compound in the form of a crystalline or amorphous salt or any combination thereof, where the counterion is selected from pharmaceutically acceptable water-soluble organic or inorganic acids. The present invention also relates to frozen preparations containing a class III antiarrhythmic compound in the form of a salt solution, where the counterion is selected from pharmaceutically acceptable water-soluble organic or inorganic acids. Preferred preparations contain a salt of the compound 3,7-diazabicyclo[3.3.1]-nonane-3-carboxylic acid, 7-[(2S)-3-(4-cyanophenoxy)-2-hydroxypropyl]-1,1-dimethylethyl ester (Compound A). Further aspects of the present invention include salts of Compound A per se, processes for preparing the preparations, as well as use of the preparations for prophylaxis and/or treatment of cardiac arrhytmia.

32 Claims, No Drawings

DRIED OR FROZEN PHARMACEUTICAL PREPARATION CONTAINING A CLASS III ANTIARRHYTHMIC COMPOUND

This application is a 371 of PCT/SE 99/01828, filed Oct. 11, 1999.

FIELD OF THE INVENTION

The present invention relates to dried preparations containing a class III antiarrhythmic compound in the form of a crystalline or amorphous salt or any combination thereof, where the counterion is selected from pharmaceutically acceptable water-soluble organic or inorganic acids. The present invention also relates to frozen preparations containing a class III antiarrhythmic compound in the form of a salt solution, where the counterion is selected from pharmaceutically acceptable water-soluble organic or inorganic acids. Preferred preparations contain a salt of the compound 3,7-diazabicyclo[3.3.1]-nonane-3-carboxylic acid, 7-[(2S)-3-(4-cyanophenoxy)-2-hydroxypropyl]-1,1-dimethylethyl ester (hereinafter Compound A). Further aspects of the present invention include salts of Compound A per se, processes for preparing the preparations, as well as use of the preparations for prophylaxis and/or treatment of cardiac arrhytmia.

BACKGROUND OF THE INVENTION

Cardiac arrhythmias may be defined as abnormalities in the rate, regularity, or site of origin of the cardiac impulse or as disturbances in conduction which causes an abnormal sequence of activation.

Arrhythmias may be classified clinically by means of the presumed site of origin (i.e. as supraventricular, including atrial and atrioventricular arrhythmias and ventricular arrhythmias) and/or by means of rate (i.e. bradyarrhythmias (slow) and tachyarrhythmias (fast)).

In the treatment of cardiac arrhythmias, the negative outcome in some clinical trials (see, for example, the outcome of the Cardiac Arrhythmia Suppression Trial (CAST) reported in New England Journal of Medicine, 321, 406 (1989)) with drugs, acting primarily by slowing the conduction velocity (class I antiarrhythmic drugs), has prompted drug development towards compounds which selectively delay cardiac repolarization, thus prolonging the QT interval of the ECG. Class III antiarrhythmic drugs may be defined as drugs which prolong the action potential duration (which can be caused by a block of outward $K^+$ currents or from an increase of inward ion currents) and refractoriness, without affecting cardiac conduction.

One of the key disadvantages of hitherto known drugs which act by delaying repolarization (class III or otherwise) is that they all are known to induce a unique form of proarrhythmia known as torsades de pointes, which may, on occasion be fatal. From the point of view of safety, the minimisation of this phenomenon (which has also been shown to be exhibited as a result of administration of non-cardiac drugs such as phenothiazines, tricyclic antidepressants, antihistamines and antibiotics) is a key problem to be solved in the provision of effective antiarrhythmic drugs.

Most antiarrhythmic drugs (including class III antiarrhythmic drugs) have a duration of action of between 3 and 12 hours. For example, the selective class III antiarrhythmic drug ibutilide (Pharmacia & Upjohn) has a half-life of elimination, which averages at around 6 hours when the drug is administered intravenously to a human patient.

In the minimisation of the side effects (including torsades de pointes) associated with anti-arrhythmic drugs, compounds which are effective, yet short acting, when administered intravenously, are expected to be of benefit. Accordingly, compounds which have a duration of action which is relatively short (hereinafter referred to as "short acting compounds") may be expected to have clinical advantages when used in the acute conversion of arrhythmias, including reduced monitoring and hospitalisation time.

The class III antiarrhythmic compounds of the present invention, including Compound A, are such short acting compounds useful in the prophylaxis and treatment of cardiac arrhythmias. Their properties and the preparation thereof are described in International Patent Application WO 99/31100 that is hereby incorporated by reference.

Compound A is poorly soluble in water and unstable in water solutions. Compound A can thus not be readily formulated as a ready-for-use aqueous solution.

The physico-chemical properties of the class III antiarrhythmic compounds of the present invention, including Compound A (which is a weak base), such as low water solubility and decomposition in water solution, especially at a low pH, provide difficulties in formulating pharmaceutical preparations containing these compounds which are stable during storage and easy to administer, e.g. parenterally in a suitable volume.

In addition of being unphysiologically low, the pH of the acidic solution makes the active substance decompose and thus the storage stability of the solution will be insufficient.

Thus, an objective of the present invention is to provide pharmaceutical preparations containing certain class III antiarrhythmic compounds having good storage stability.

A further objective of the invention is to provide a parenteral pharmaceutical preparation of Compound A having good storage stability and which can be easily administered as a solution to mammals.

A still further objective of the invention is to provide a method of preparing such a parenteral pharmaceutical preparation.

SUMMARY OF THE INVENTION

One aspect of the invention relates to a dried pharmaceutical preparation for preparation of a solution ex tempore comprising a class III antiarrhythmic compound of the general formula

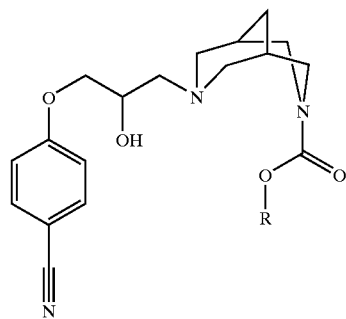

wherein
R represents linear, branched, cyclic or acyclic $C_{1-6}$ alkyl, in the form of a crystalline or amorphous salt or any combination thereof, wherein the counterion is selected from an acid which is a pharmaceutically acceptable water-soluble organic or inorganic acid.

Another aspect of the invention relates to a frozen, aqueous pharmaceutical preparation comprising a class III antiarrhythmic compound of the general formula

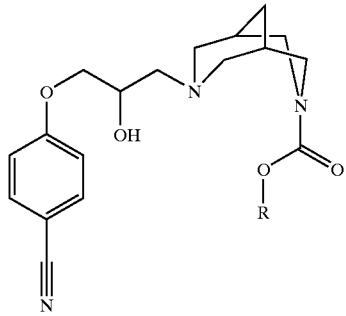

wherein
R represents linear, branched, cyclic or acyclic $C_{1-6}$ alkyl, in the form of a salt solution, wherein the counterion is selected from an acid which is a pharmaceutically acceptable water-soluble organic or inorganic acid.

Yet another aspect of the invention relates to a process for the preparation of a dried or frozen pharmaceutical preparation containing the class III antiarrhythmic compound of the invention, comprising dissolving the class III antiarrhythmic compound in the acid and water, optionally adjusting the pH with an alkalising agent and drying or freezing, respectively, the resulting solution.

Still another aspect of the invention relates to a salt of the compound 3,7-diazabicyclo[3.3.1]nonane-3-carboxylic acid, 7-[(2S)-3-(4-cyanophenoxy)-2-hydroxypropyl]-1,1-dimethylethyl ester, a salt of the compound 3,7-diazabicyclo[3.3.1]nonane-3-carboxylic acid, 7-[(2R)-3-(4-cyanophenoxy)-2-hydroxypropyl]-1,1-dimethylethyl ester or any mixture thereof, wherein the counterion is selected from an acid which is a pharmaceutically acceptable water-soluble organic or inorganic acid, suitably tartaric acid.

A further aspect of the invention relates to use of a salt or salt solution of a class III antiarrhythmic compound according to the invention in the manufacture of a dried or frozen pharmaceutical preparation for the prophylaxis and/or treatment of cardiac arrhythmia.

A still further aspect of the invention relates to a method for the prophylaxis and/or treatment of cardiac arrhythmia, especially atrial and ventricular arrhythmia, wherein a pharmaceutical preparation according to the present invention is administered to a mammal in the need of such prophylaxis and/or treatment after reconstitution and optional dilution or thawing and optional dilution.

DETAILED DESCRIPTION OF THE INVENTION

It has now been found that the solubility of the active substance and the storage stability of a pharmaceutical preparation, of a class III antiarrhythmic compound of the present invention, especially parenteral preparations of Compound A, can be considerably improved by dissolving the active substance in water together with a water-soluble organic or inorganic acid, and by optionally adjusting the pH to a physiologically acceptable level where the substance remains dissolved, followed by drying, especially freeze-drying, of the obtained solution to yield a dry salt or salt mixture or freezing the obtained solution.

The salts of the present invention can be crystalline or amorphous or any combination thereof, preferably amorphous.

In a particularly preferred embodiment, the pharmaceutical preparation according to the present invention is a parenteral formulation comprising Compound A in the form of an amorphous salt, after freeze-drying of a water solution of the stable base of Compound A dissolved in an acid. An alternative to freeze-drying is to store the solution frozen. The freeze-dried product is reconstituted and optionally diluted before administration. The frozen product is thawed and optionally diluted before administration.

The present invention also relates to dry mixtures of a class III antiarrhythmic compound and a pharmaceutically acceptable water-soluble organic or inorganic acid.

The most preferred class III antiarrhythmic compound for use in the present preparations is 3,7-diazabicyclo[3.3.1]nonane-3-carboxylic acid, 7-[(2S)-3-(4-cyanophenoxy)-2-hydroxy-propyl]-1,1-dimethylethyl ester (Compound A).

Although the present invention relates to preparations comprising various class III anti-arrhythmic compounds, in the following the invention will be described with reference to Compound A only.

The acid used to dissolve the Compound A is a pharmaceutically acceptable, water-soluble inorganic or organic acid. Salts which may be mentioned include acid addition salts.

Suitable inorganic acids are hydrochloric acid, hydrobromic acid, sulphuric acid and phosphoric acid.

Suitable organic acids are sulphonic acids (such as methanesulphonic acid, bensenesulphonic acid, p-toluene sulphonic acid, 2-ethane sulphonic acid, and 2-hydroxy ethane sulphonic acid), carboxylic acids (such as aspartic acid, maleic acid, succinic acid, malonic acid, acetic acid, fumaric acid, bensoic acid and hydroxy bensoic acid), and hydroxy acids (such as salicylic acid, glycolic acid, malic acid, ascorbic acid, citric acid, gluconic acid, lactic acid and tartaric acid).

Properties of the acid, such as the water solubility, lipophilicity and dissociation constants determine the suitability as acidic additive and the amount of acid to be used. In the present invention, water-soluble means that the amount of acid necessary for ionizing Compound A is soluble in the volume of water used in the preparation of the preparation.

Mono as well as polyvalent acids can be used to dissolve the active substance in water.

The preferred acid is tartaric acid.

The present invention also relates to a salt of the compound 3,7-diazabicyclo[3.3.1]nonane-3-carboxylic acid, 7-[(2S)-3-(4-cyanophenoxy)-2-hydroxypropyl]-1,1-dimethylethyl ester, a salt of the compound 3,7-diazabicyclo[3.3.1]nonane-3-carboxylic acid, 7-[(2R)-3-(4-cyanophenoxy)-2-hydroxypropyl]-1,1-dimethylethyl ester, or any mixture thereof, wherein the counterion is selected from an acid which is a pharmaceutically acceptable water-soluble organic or inorganic acid.

Preferred salts are the tartrate salts of 3,7-diazabicyclo[3.3.1]nonane-3-carboxylic acid, 7-[(2S)-3-(4-cyanophenoxy)-2-hydroxypropyl]-1,1-dimethylethyl ester, the tartrate salts of 3,7-diazabicyclo[3.3.1]nonane-3-carboxylic acid, 7-[(2R)-3-(4-cyanophenoxy)-2-hydroxypropyl]-1,1-dimethylethyl ester, or any mixture thereof.

The mixtures of enantiomers of the present invention include the racemic mixture, i.e. a 50:50 mixture of the (S) and (R) enantiomers.

The most preferred salts are the tartrate salts of the compound 3,7-diazabicyclo[3.3.1]nonane-3-carboxylic acid, 7-[(2S)-3-(4-cyanophenoxy)-2-hydroxypropyl]-1,1-dimethylethyl ester.

After dissolving Compound A in an aqueous acid solution, a low pH of the solution gives rise to enhanced degradation of Compound A. This may cause poor stability of Compound A during preparation and filling as well as during storage before administration. A low pH is also unphysiologic for parenteral use. Therefore, the pH of the solution may be adjusted by an alkalising agent to a value in the range of pH 3 to pH 7.4 (physiological pH), depending on at what concentration the compound is dissolved. The concentration should be below the solubility limit of the active substance at that pH.

In order to obtain suitable volumes for dosing, the concentration of Compound A is preferably in the range of 0.1 to 45.0 mg/ml in a stock solution before drying, preferably freeze-drying, or freezing. Preferably a stock solution containing 25 mg/ml of Compound A is adjusted to a pH value from 3.5 to 4.5.

A suitable alkalising agent for the optional pH adjustment is an agent such as sodium hydroxide, potassium hydroxide, sodium carbonate, potassium carbonate, sodium bicarbonate, potassium bicarbonate, ammonia, and sodium tartrate.

The pharmaceutical preparation of the invention may be manufactured in the following way. The active substance is dissolved in an aqueous acid solution and sterile water is added. Optionally, the pH is adjusted and, if necessary, further water is added to reach the final weight. Finally, the pH is controlled and adjusted if necessary. The solution is suitably sterile filtered, filled into primary packages, such as vials, cartridges, prefilled syringes and dried, suitably freeze-dried, or frozen.

In the present invention, any order of mixing the active substance, acid and water can be used. Suitably, the acid is mixed with water to make up an acid solution before the active substance is dissolved in said acid solution. In this way, the degradation of the compound can be minimized. The use of excess acid in a water solution, followed by pH adjustment with an alkalising agent after dissolution of the active substance, allow a quick dissolution process while still exposing the active substance to a tolerable pH range.

In the present invention, the drying process can be any suitable process that removes the water while maintaining the integrity of the class III antiarrhythmic compound. Freeze-drying is preferred. The degradation rate of Compound A is temperature dependent and the temperature of a water solution of Compound A should not exceed about 25° C. to avoid degradation.

Before administration the dried, suitably freeze-dried, or frozen product is reconstituted and/or diluted in for instance water, physiological saline, glucose solution or any other suitable solution. The frozen solution is thawed, optionally diluted with for instance any of the above mentioned solutions.

In the first part of the process to obtain the preferred preparation comprising the tartrate of Compound A, tartaric acid is added to Compound A providing good solubility of Compound A.

Optionally, in the following part of the process to obtain the preparation, an adjustment of pH by addition of an alkalising agent to the solutions of Compound A provides a physiologically acceptable pH and enhanced stability (reduced degradation) of Compound A.

In the further part of the process to obtain the preparation, freezing or drying, preferably freeze-drying, a solution of Compound A and tartaric acid provides a preparation with good storage stability. The use of freeze-dried tartrate of Compound A provides very good storage stability.

The pharmaceutical preparation according to the invention is used for the treatment and/or prophylaxis of cardiac arrhythmias, preferably atrial and ventricular arrhythmia and most preferably atrial fibrillation.

The pharmaceutical preparation according to the invention is normally administered parenterally including but not restricted to intravenously, intraarterially, intranasally, subcutaneously, intracutaneously, intramuscularly, intralipomateously, intraperitoneally, buccally or by inhalation.

Suitable parenteral doses for Compound A in the therapeutical treatment of mammals, including man, are from 0.05 to 5 mg/kg of body weight.

The preparation of the present invention, suitably further contains adjuvants, carriers and/or diluents.

The preparation according to the invention may contain ingredients besides those mentioned above. Such ingredients may be antimicrobial preservatives, tonicity modifiers and/or antioxidants.

The preparations of the present invention may contain additional salts, which may be added or formed in the process. An example of the latter is sodium tartrate, which may be formed in the process of preparing a tartrate salt of e.g. Compound A.

A specific salt that may be used to advantage in the present preparations is sodium chloride. Thus, especially in the frozen, aqueous preparations sodium chloride is suitably used to make the preparations isotonic.

EXAMPLES

The following Examples are intended to illustrate, but in no way limit the scope of the invention.

Preparation of Compound A

A. 4-[(2S)-Oxiranylmethoxy]benzonitrile (R)-(-)-Epichlorohydrin (800 mL) and $K_2CO_3$ (414 g) were added to a stirred solution of p-cyanophenol (238 g) in 2.0 L MeCN and the reaction mixture was refluxed under inert atmosphere for 2 h. The hot solution was filtered and the filtrate concentrated giving a clear oil which was crystallized from diisopropyl ether giving the product in 90% yield.

B. tert-Butyl 3.7-diazabicyclo[3.3.1]nonane-3-carboxylate (a) tert-Butyl 7-benzyl-9-oxy-3,7-diazabicyclo[3.3.1]nonane-3-carboxylate Paraformaldehyde (4.00 g; 127 mmol) was added to a solution of benzylamine (13.7 g; 126 mmol) in ethanol (190 mL). The solution was heated to 60° C. and a solution of acetic acid (15.2 g; 252 mmol) in ethanol (160 mL) was added over 2 hours. After additional stirring for 1 hour; the solution was cooled to room temperature. This solution was added (over 2 hours) to a mixture of 1-tert-butoxycarbonyl-4-piperidone (25.5 g; 127 mmol) and para-formaldehyde (4.80 g; 152 mmol) in ethanol (270 mL) which had been heated to 60° C. After reflux overnight, the solution was cooled to room temperature. The ethanol was removed by evaporation. Extractive work-up was performed in toluene:water and the material was filtered through silica in a toluene:ethyl acetate system. Evaporation of the eluate gave a solid material (37.4 g). The purity was 90 area % (HPLC) and the yield was 60%. By performing a crystallisation in isopropanol, a compound with a purity of 98 area % (HPLC) and a yield of 70% was obtained.

MS (EI; 70 eV): m/z 91 (100%), m/z 57 (42%), m/z 273 (32%), m/z 330 (5%); $^{13}C$ NMR ($CDCl_3$): Λ 28.72, 47.71, 49.91, 50.60, 58.83, 59.16, 61.96, 80.18, 127.37, 128.45, 128,89. 137.57, 154.89, 213.66 ppm using TMS as reference.

(b) tert-Butyl 7-benzyl-3.7-diazabicyclo[3,3,1]-nonane-3-carboxylate

A mixture of 4-toluenesulfonehydrazide (12.4 mmol; 2.30 g) and tert-butyl 7-benzyl-9-oxy-3,7-diazabicyclo[3.3.1]nonane-3-carboxylate (10.1 mmol; 4.00 g; 83.3%; from step (a) above) were dissolved in isopropanol (30 mL) and heated at reflux for 2 hours. Acetic acid (2.5 mmol; 0.15 g) and sodium cyanoborohydride (12.1 mmol, 0.76 g) were added and the mixture was again heated at reflux for 2 hours. The slurry was cooled to ambient temperature and filtered. The filtrate was concentrated and an extractive work-up was performed in toluene:water. The toluene solution was concentrated to give 0.95 g of sub-title compound, with a purity of 90 area % (GC) in a yield of 60%.

MS (EI; 70 eV): m/z 259 (100%), m/z 91 (95%), m/z 169 (45%), m/z 57 (35%), m/z 316 (25%); $^{13}$C NMR (CDCl$_3$): 28.67, 28.95, 31.11, 47.55, 48.38, 58.70, 58.96, 63.46, 78.71, 126.57, 128.00, 128.53, 138.94, 155.20 ppm using TMS as a reference (c) tert-Butyl 3,7-diazabicyclo[3.3.1]nonane-3-carboxylate tert-Butyl 7-benzyl-3,7-diazabicyclo[3.3.1]nonane-3-carboxylate (from step (b) above) was debenzylated by catalytic hydrogenation in ethanol over 5% Pd/C, at 1 atm. When the theoretical amount of H2-gas had been consumed, the catalyst was removed by filtration through a pad of celite. The residue was evaporated to give the title compound in quantitative yield.

$^{13}$C NMR (CDCl$_3$): δ 28.05, 28.29, 31.33, 48.35, 49.11, 51.53, 79.34, 155.16.

C. 3.7-Diazabicyclo[3.3.1]nonane-3-carboxylic Acid, 7-[(2S)-3-(4-cyano-phenoxy)-2-hydroxypropyl]-1,1-dimethylethyl Ester [Compound A]

4-[(2S)-Oxiranylmethoxy]benzonitrile (5.19 g; 29.6 mmol; see A above) was added to a stirred solution of tert-butyl 3,7-diazabicyclo[3.3.1]nonane-3-carboxylate (6.7 g; 29.6 mmol; see B above) in IPA (30 mL) and H$_2$O (3 mL) The reaction mixture was stirred at 60° C. for 12 h and then at rt for 48 h. The reaction mixture was concentrated, the residue dissolved in DCM, dried (MgSO$_4$) and concentrated. The residue was purified using column chromatography (hexane:EtOAc:MeOH; 50:45:5) to give the title product as a white foam in a 56% yield (6.65 g).

$[\alpha]_{20}^D$=16 (c=1.0; MeOH). ESI-MS (M+1)$^+$ 402 (m/z); $^{13}$C NMR (CDCl$_3$): δ 28.44, 28.77, 29.33, 31.93,47.53, 49.34, 56.87, 60.14, 61.60, 65.03, 70.70, 79.37, 103.85, 115.32, 119.13, 133.79, 155.91, 162.16.

Working Examples

Example 1

A preparation having the following composition was prepared:

| | | |
|---|---|---|
| Compound A | 25 mg | |
| Tartaric acid | 9.35 mg | |
| Sodium hydroxide to pH 4 | q.s. | |
| Water to | 1.0 ml | |

The formulation was prepared by dissolving Compound A in tartaric acid (0.1 M) during stirring. Water for injection was added. pH was adjusted to 4 by addition of sodium hydroxide (0.1 M). Water to final weight was added. pH was controlled and adjusted again if necessary. The solution was sterile filtered through a 0.22 μm membrane filter. The sterile solution was filled into vials and the formulation was freeze-dried. The vials were sealed in the freeze-dryer equipment under nitrogen atmosphere.

Examples 2–7

The active substances were dissolved in acid (0.1 M–1 M), water was added and pH was adjusted with alkalising agent. Water was added to final weight. The solutions were stored frozen.

Compositions:

| | | |
|---|---|---|
| 2) | Compound A | 10 mg |
| | tartaric acid (⅔ equimolar) | 2.5 mg |
| | ammonia solution | q.s. to pH 4 |
| | water | to 1.0 ml |
| 3) | Compound A | 12 mg |
| | tartaric acid (equimolar) | 4.48 mg |
| | potassium hydroxide 0.1 M | q.s. to pH 5 |
| | water | to 1.0 ml |
| 4) | Compound A | 450 mg |
| | tartaric acid (equimolar) | 167 mg |
| | sodium hydroxide 0.01 M | q.s. to pH 4 |
| | water | to 1.0 ml |
| 5) | Compound A | 250 mg |
| | hydrochloric acid 1 M | 0.62 g |
| | (5 × equimolar) | |
| | sodium hydroxide 0.1 M | q.s. to pH 4 |
| | water | to 1.0 ml |
| 6) | Compound A | 1 mg |
| | tartaric acid (equimolar) | 0.37 mg |
| | sodiumbicarbonate 0.1 M | q.s. to pH 4 |
| | water | to 1.0 ml |
| 7) | Compound A | 0.1 mg |
| | tartaric acid (equimolar) | 0.037 mg |
| | sodiumbicarbonate 0.5 M | q.s. to pH 6 |
| | water | to 1.0 ml |
| 8) | Racemate of compound A | 25 mg |
| | tartaric acid | 9.35 mg |
| | sodium hydroxide | q.s. to pH 4 |
| | water | to 1.0 ml |

Examples 9–17

In a similar manner as described in Example 1 (but with respective acid at a suitable concentration) formulations having the following compositions were prepared and freeze-dried:

| | | |
|---|---|---|
| 9) | Compound A | 25 mg |
| | Citric acid | 13 mg |
| | sodium hydroxide to pH 4 | q.s. |
| | water | to 1.0 ml |
| 10) | Compound A | 25 mg |
| | Methanesulphonic acid | 6 mg |
| | sodium hydroxide to pH 4 | q.s. |
| | water | to 1.0 ml |
| 11) | Compound A | 25 mg |
| | Fumaric acid | 28 mg |
| | sodium hydroxide to pH 4 | q.s. |
| | water | to 1.0 ml |
| 12) | Compound A | 25 mg |
| | Hydrochloric acid | 2.2 mg |
| | sodium hydroxide to pH 4 | q.s. |
| | water | to 1.0 ml |
| 13) | Compound A | 25 mg |
| | Phosphoric acid | 9.1 mg |
| | sodium hydroxide to pH 4 | q.s. |

-continued

| | | |
|---|---|---|
| | water | to 1.0 ml |
| 14) | Compound A | 25 mg |
| | Acetic acid | 11.2 mg |
| | sodium hydroxide to pH 4 | q.s. |
| | water | to 1.0 ml |
| 15) | Compound A | 25 mg |
| | Lactic acid | 9.2 mg |
| | sodium hydroxide to pH 4 | q.s. |
| | water | to 1.0 ml |
| 16) | Compound A | 25 mg |
| | Malic acid | 21.7 mg |
| | sodium hydroxide to pH 4 | q.s. |
| | water | to 1.0 ml |
| 17) | Compound A | 25 mg |
| | 2,5-dihydroxy-bensoic acid | 14.4 mg |
| | sodium hydroxide to pH 4 | q.s. |
| | water | to 1.0 ml |

Storage Stability Test

The storage stability of freeze-dried preparations and frozen solutions according to the invention have been followed for 12 months. The performed tests have demonstrated that the preparations containing the amorphous salt are stable over this period of time.

What is claimed is:

1. A dried pharmaceutical preparation comprising a class III antiarrhythmic compound of the general formula

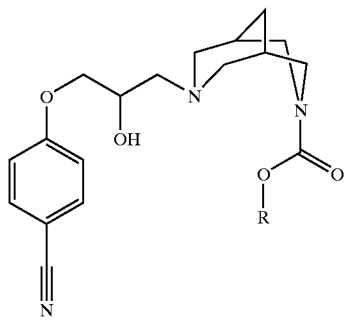

wherein

R represents linear, branched, cyclic or acyclic $C_{1-6}$ alkyl, in the form of a crystalline or amorphous salt of the compound or any combination thereof, wherein the counterion associated with the compound is an acid which is a pharmaceutically acceptable water-soluble acid.

2. The pharmaceutical preparation according to claim 1, wherein the preparation is freeze-dried.

3. The pharmaceutical preparation according to claim 1, comprising at least one additional salt.

4. The pharmaceutical preparation according to claim 1, further comprising physiological saline or a glucose solution.

5. A frozen, aqueous pharmaceutical preparation comprising a class III antiarrhythmic compound of the general formula

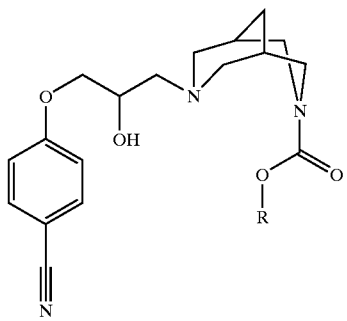

wherein

R represents linear, branched, cyclic or acyclic $C_{1-6}$ alkyl, in the form of a salt solution of the compound, wherein the counterion associated with the compound is an acid which is a pharmaceutically acceptable water-soluble acid.

6. The pharmaceutical preparation according to claim 5, comprising at least one additional salt.

7. The pharmaceutical preparation according to claim 1 or 5, wherein the class III antiarrhythmic compound is 3,7-diazabicyclo[3.3.1]nonane-3-carboxylic acid, 7-[(2S)-3-(4-cyanophenoxy)-2-hydroxypropyl]-1,1-dimethylethyl ester, or 3,7-diazabicyclo[3.3.1]nonane-3-carboxylic acid, 7[(2R)-3-(4-cyanophenoxy)-2-hydroxypropyl]-1,1-dimethylethyl ester or any mixture thereof.

8. The pharmaceutical preparation according to claim 7, wherein the class III antiarrhythmic compound is 3,7-diazabicyclo[3.3.1]nonane-3-carboxylic acid, 7-[(2S)-3-(4-cyanophenoxy) 2-hydroxypropyl]-1,1-dimethylethyl ester.

9. The pharmaceutical preparation according to claim 1 or 5, wherein the pharmaceutically acceptable water-soluble acid is selected from the group consisting of hydrochloric acid, hydrobromic acid, sulphuric acid, phosphoric acid, a sulphonic acid, a carboxylic acid and a hydroxy acid.

10. The pharmaceutical preparation according to claim 9, wherein the acid is a hydroxy acid.

11. The pharmaceutical preparation according to claim 10, wherein the hydroxy acid is tartaric acid.

12. The pharmaceutical preparation according to claim 1 or 5, wherein the salt is a tartrate salt of 3,7-diazabicyclo[3.3.1]nonane-3-carboxylic acid, 7-[(2S)-3-(4-cyanophenoxy)-2-hydroxypropyl]-1,1-dimethylethyl ester, a tartrate salt of 3,7-diazabicyclo[3.3.1]nonane-3-carboxylic acid, 7-[(2R)-3-(4-cyanophenoxy)-2-hydroxypropyl]-1,1-dimethylethyl ester or any mixture thereof.

13. The pharmaceutical preparation according to claim 12, wherein the salt is a tartrate salt of the compound 3,7-diazabicyclo[3.3.1]nonane-3-carboxylic acid, 7-[(2S)-3-(4-cyanophenoxy)-2-hydroxypropyl]-1,1-dimethylethyl ester.

14. The pharmaceutical preparation according to claim 1 or 5, further comprising an alkalising agent.

15. The pharmaceutical preparation according to claim 14, wherein the alkalising agent is selected from the group consisting of sodium hydroxide, potassium hydroxide, sodium carbonate, potassium carbonate, sodium bicarbonate, potassium bicarbonate, ammonia and sodium tartrate.

16. A process for the preparation of a dried pharmaceutical preparation comprising a class III antiarrhythmic compound of the general formula

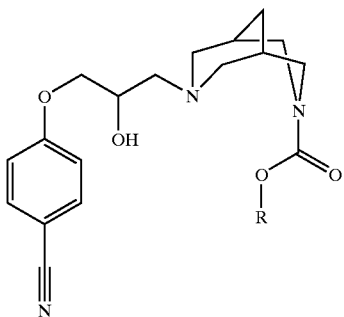

wherein

R represents linear, branched, cyclic or acyclic $C_{1-6}$ alkyl, in the form of a crystalline or amorphous salt of the compound or any combination thereof, wherein the counterion associated with the compound is an acid which is a pharmaceutically acceptable water-soluble acid, and wherein the process comprises dissolving the class III antiarrhythmic compound in an aqueous solution of the acid, optionally adjusting the pH with an alkalising agent and drying the resulting solution.

17. The process according to claim 16, wherein the preparation is freeze-dried.

18. A process for the preparation of a frozen, aqueous pharmaceutical preparation comprising a class III antiarrhythmic compound of the general formula

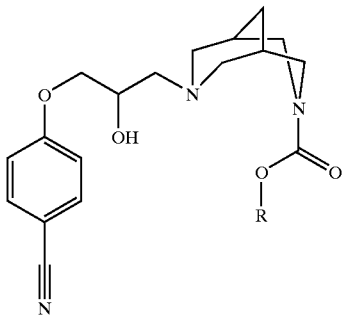

wherein

R represents linear, branched, cyclic or acyclic $C_{1-6}$ alkyl, in the form of a salt solution of the compound, wherein the counterion associated with the compound is an acid which is a pharmaceutically acceptable water-soluble acid, and wherein the process comprises dissolving the class III antiarrhythmic compound in an aqueous solution of the acid, optionally adjusting the pH with an alkalising agent and freezing the resulting solution.

19. The process according to claim 16 or 18, wherein the class III antiarrhythmic compound is 3,7-diazabicyclo[3.3.1]nonane-3-carboxylic acid, 7-[(2S)-3-(4-cyanophenoxy)-2-hydroxypropyl]-1,1-dimethylethyl ester, or 3,7-diazabicyclo[3.3.1]nonane-3-carboxylic acid, 7-[(2R)-3-(4-cyanophenoxy)-2-hydroxypropyl]-1,1-dimethylethyl ester, or any mixture thereof.

20. The process according to claim 19, wherein the class III antiarrhythmic compound is 3,7-diazabicyclo[3.3.1]nonane-3-carboxylic acid, 7-[(2S)-3-(4-cyanophenoxy)-2-hydroxypropyl]-1,1-dimethylethyl ester.

21. The process according to claim 16 or 18, wherein the pharmaceutically acceptable water-soluble acid is selected from the group consisting of hydrochloric acid, hydrobromic acid, sulphuric acid, phosphoric acid, sulphonic acids, carboxylic acids and hydroxy acids.

22. The process according to claim 16 or 18, wherein the pH is adjusted to a pH in the range of from 3 to 7.4.

23. A salt of the compound 3,7-diazabicyclo[3.3.1]nonane-3-carboxylic acid, 7-[(2S)-3-(4-cyanophenoxy)-2-hydroxypropyl]-1,1-dimethylethyl ester, or a salt of the compound 3,7-diazabicyclo[3.3.1]nonane-3-carboxylic acid, 7-[(2R)-3-(4-cyanophenoxy)-2-hydroxypropyl]-1,1-dimethylethyl ester, or any mixture thereof, wherein the counterion associated with the compound is an acid which is a pharmaceutically acceptable water-soluble acid.

24. A tartrate salt of 3,7-diazabicyclo[3.3.1]nonane-3-carboxylic acid, 7-[(2S)-3-(4-cyanophenoxy)-2-hydroxypropyl]-1,1-dimethylethyl ester, a tartrate salt of 3,7-diazabicyclo[3.3.1]nonane-3-carboxylic acid, 7-[(2R)-3-(4-cyanophenoxy)-2-hydroxypropyl]-1,1-dimethylethyl ester, or any mixture thereof.

25. A tartrate salt of the compound 3,7-diazabicyclo[3.3.1]nonane-3-carboxylic acid, 7-[(2S)-3-(4-cyanophenoxy)-2-hydroxypropyl]-1,1-dimethylethyl ester.

26. A method for the prophylaxis and/or treatment of cardiac arrhythmia, wherein a dry pharmaceutical preparation according to claim 1 is reconstituted and/or diluted and subsequently administered to a mammal in need of such prophylaxis and/or treatment.

27. A method for the prophylaxis and/or treatment of cardiac arrhythmia, wherein a frozen pharmaceutical preparation according to claim 5 is thawed, optionally diluted, and subsequently administered to a mammal in need of such prophylaxis and/or treatment.

28. The method according to claim 26 or 27 for the prophylaxis and/or treatment of atrial and ventricular arrhythmia.

29. The method according to claim 26 or 27 for the prophylaxis and/or treatment of atrial fibrillation.

30. The method according to claim 26 or 27, wherein the preparation is administered intravenously, intraarterially, intranasally, subcutaneously, intracutaneously, intramuscularly, intralipomateously, intraperitoneally, buccally or by inhalation.

31. The pharmaceutical preparation according to claim 3 or 6, wherein the additional salt is sodium chloride.

32. The method according to claim 26 or 27, wherein the class III antiarrhythmic compound is 3,7-diazabicyclo[3.3.1]nonane-3-carboxylic acid, 7-[(2S)-3-(4-cyanophenoxy)-2-hydroxypropyl]-1,1-dimethylethyl ester, or 3,7-diazabicyclo[3.3.1]nonane-3-carboxylic acid, 7-[(2R)-3-(4-cyanophenoxy)-2-hydroxypropyl]-1,1-dimethylethyl ester or any mixture thereof, in the form of a salt or salt solution of the compound, wherein the counterion associated with the compound is an acid which is a pharmaceutically acceptable water-soluble acid.

* * * * *